United States Patent [19]

McGrath et al.

[11] Patent Number: 5,086,156

[45] Date of Patent: * Feb. 4, 1992

[54] PHOSPHORUS CONTAINING EPOXY NETWORKS BASED ON TRIHYDROCARBYL PHOSPHINE OXIDES HAVING ACTIVE SUBSTITUENTS

[75] Inventors: James E. McGrath; Attila Gungor, both of Blacksburg, Va.

[73] Assignee: Virginia Tech Intellectual Properties, Inc., Blacksburg, Va.

[*] Notice: The portion of the term of this patent subsequent to Nov. 27, 2007 has been disclaimed.

[21] Appl. No.: 592,415

[22] Filed: Oct. 3, 1990

Related U.S. Application Data

[63] Continuation-in-part of Ser. No. 418,066, Oct. 6, 1989, Pat. No. 4,973,631.

[51] Int. Cl.⁵ .................... C08G 59/30; C08G 59/62
[52] U.S. Cl. ................................. 528/108; 528/391; 528/398; 528/399; 525/534

[58] Field of Search ............... 528/108, 391, 398, 399; 525/534

[56] References Cited

U.S. PATENT DOCUMENTS

| | | | |
|---|---|---|---|
| 3,415,779 | 12/1968 | Preininger et al. | 528/398 X |
| 4,072,653 | 2/1978 | Moedritzer et al. | 528/398 X |
| 4,298,709 | 11/1981 | Ginter et al. | 528/108 X |
| 4,345,059 | 8/1982 | Fretz et al. | 528/108 X |
| 4,587,324 | 5/1986 | Mikroyannidis et al. | 528/399 X |
| 4,973,631 | 11/1990 | McGrath et al. | 528/108 X |

*Primary Examiner*—John Kight, III
*Assistant Examiner*—Frederick Krass
*Attorney, Agent, or Firm*—Richard P. Fennelly; Louis A. Morris

[57] ABSTRACT

Epoxy resins can be cured or crosslinked with trihydrocarbyl phosphine oxide compounds having epoxy-reactive (active hydrogen) substituents either alone or in combination with amine-terminated polyarylene ethers (e.g., amine-terminated polysulfone oligomers or high polymers.

5 Claims, No Drawings

PHOSPHORUS CONTAINING EPOXY NETWORKS BASED ON TRIHYDROCARBYL PHOSPHINE OXIDES HAVING ACTIVE SUBSTITUENTS

This is a continuation-in-part of U.S. Ser. No. 418,066, filed Oct. 6, 1989, now U.S. Pat. No. 4,973,631.

BACKGROUND OF THE INVENTION

Novel, high performance, phosphorus containing epoxy networks have been prepared and characterized using 1, for example, as the crosslinking moiety, and also using 1 in conjunction with amine terminated polyarylene ethers, such as polysulfone, as the crosslinking reagents. These formulations are useful as flame retardant epoxy networks. They also provide a method of toughening the otherwise brittle cured materials.

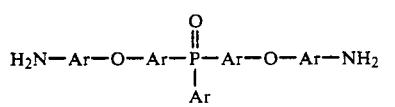
(1)

The chain extender, 1, can be prepared according to Scheme 1, X = Cl or F. The reaction medium can be a 75:25 vol/vol mixture of dimethylacetamide and toluene (10–12% solids or higher in the reaction medium). Nitrogen atmosphere and 2.05 moles of potassium carbonate can be employed. The phosphorus dihalide monomer and aminophenol can be charged to a reaction vessel equipped with an agitator, nitrogen inlet, and condenser with a Dean Stark trap for water removal. Both dimethylacetamide and toluene are preferably previously dried over calcium hydride, distilled, and maintained under inert atmosphere. The reaction solvents, then the potassium carbonate can be charged, and the temperature is brought up to the reaction temperature. Where X = F, optimum conditions for the reaction

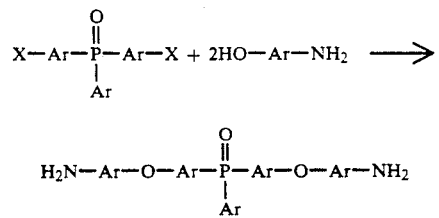

are 140° C. for a fourteen hour period. The crude yield of this reaction is nearly quantitative, e.g., about 93%. When X = Cl, the optimum conditions are 160° C. for a period of thirty-six hours and the crude yield is about 60%. Following completion of the reaction, toluene and excess dimethylacetamide can be vacuum stripped from the system until a 30–35% solution of the product in dimethylacetamide is obtained. The product crystallizes in this solution over approximately a six hour period. They are filtered, washed, dried at 60° C. under vacuum, then recrystallized from dimethylacetamide. Finally the recrystallized material is recovered and dried under vacuum at 150° C. to a constant weight.

The instant invention, in its broadest context, involves the use of a "trihydrocarbyl phosphine oxide epoxy curing agent" which is to be understood as encompassing compounds having the preferred structure, for example, of

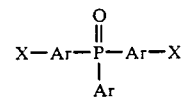

where each of the three groups can be a substituted or unsubstituted phenyl ring (Ar) with the proviso that such compounds also contain epoxy-reactive substituent(s) (shown, for example, by the moieties X). As is well known in the art, such substituents X have active hydrogen and include amine ($-NH_2$), hydroxy ($-OH$), carboxy ($-COOH$), anhydride, and thiol ($-SH$) moieties. It is preferred that two or more such substituents reside in the compound (e.g., either directly on one or more of the Ar groups or on suitable substituents, e.g., $-OAr'$, on such Ar groups). The above crosslinking agent can be used with other amine terminated polymers, if desired, for example, amine-terminated polyarylene ethers such as the polysulfone oligomers or high polymers. In a broader sense, however, one or more of the Ar groups depicted above can be substituted with another hydrocarbyl group, such as alkyl, especially the Ar group which is not substituted with substituent group "X".

EXAMPLE 1

The diglycidyl ether of bisphenol-A (1.74 gm) was charged to an aluminum mold and preheated to about 80° C. This was degassed under vacuum at 100° C. for five minutes. Monomer 1 (1.26 gm) was then charged to the mold. This mixture was agitated, then degassed a second time. The mold was brought to curing temperature, 150° C., and maintained at that temperature for 45 minutes, then, subsequently, the temperature was raised to 190° C. and maintained at this temperature for an additional forty-five minutes. The sample was cooled slowly to room temperature to produce a transparent, light yellow-green material.

EXAMPLE 2

Preparation of a cured epoxy material containing both an aromatic amine terminated polyarylether sulfone oligomer of 16,000 gm/mole (15 weight % of the final cured material) and the phosphorus containing curing reagent, 1: 0.3 gm of the aromatic amine terminated polyarylether sulfone and 0.98 gm of the diglycidyl ether of bisphenol-A were charged to an aluminum mold. This mixture was preheated to 100° C., then agitated until homogeneity was complete (about twenty-five minutes). The mixture was then degassed under vacuum at 100° C. 0.71 gm of the phosphorus containing curing agent, 1, was charged and the mixture was agitated to attain a homogeneous solution, and subsequently, degassed at 100° C. a second time (ten minutes). Curing was effected by heating at 150° C. for forty-five minutes, then at 190° C. for an additional forty-five minutes. The sample was cooled slowly to room temperature to produce a transparent, light yellow-green material.

EXAMPLE 3

Preparation of a cured epoxy material containing both an aromatic amine terminated polyarylether sulfone oligomer of 16,000 gm/mole (30% by weight of the final material) and the phosphorus containing curing reagent, 1: 0.6 gm of the aromatic amine terminated polyarylether sulfone and 0.8 gm of the diglycidyl ether of bisphenol-A were charged to an aluminum mold. This mixture was preheated to 100° C., then agitated until homogeneity was complete (about twenty-five minutes). The mixture was then degassed under vacuum at 100° C. 0.58 gm of the phosphorus containing curing agent, 1, was charged and the mixture was agitated to attain a homogeneous solution, and subsequently, degassed at 100° C. a second time (ten minutes). Curing was effected by heating at 150° C. for forty-five minutes, then at 190° C. for an additional forty-five minutes. The sample was cooled slowly to room temperature to produce a transparent, light yellow-green material.

For the 15 weight % polyarylether sulfone containing phosphone-epoxy material, samples were freeze-fractured and scanning electron photomicrographs were taken of the fracture surfaces. These micrographs indicate than an epoxy matrix is present containing polysulfone domains of about 0.8–1 μ in diameter. The 30 weight % polyarylether sulfone containing material was subjected to the same type of analysis. In these samples, the photomicrographs indicate that phase inversion has occurred. Thus, epoxy domains of 1.5–2.0 μ are present in a thin matrix of the polyarylether sulfone component.

Differential scanning calorimetry data performed at 10°/minute on the phosphone-epoxy material without any added polyarylether sulfone component, shows a glass transition of 170° C.

We claim:

1. A curable epoxy resin composition containing a curable epoxy resin and, as a curing agent, an effective amount for curing of a trihydrocarbyl phosphine oxide epoxy curing agent substituted with an active hydrogen substituent.

2. A composition as claimed in claim 1 wherein the active hydrogen substituent is —NH$_2$.

3. A composition as claimed in claim 1 wherein at least two active hydrogen substituents are contained in the curing agent.

4. A composition as claimed in claim 2 wherein the active hydrogen substituent is —OC$_6$H$_5$NH$_2$.

5. A composition as claimed in claim 1 which further comprises an amine-terminated polysulfone oligomer or high polymer.

* * * * *